(12) United States Patent
Santos et al.

(10) Patent No.: US 7,169,178 B1
(45) Date of Patent: Jan. 30, 2007

(54) STENT WITH DRUG COATING

(75) Inventors: Veronica J Santos, Ithaca, NY (US); Santosh Prabhu, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 236 days.

(21) Appl. No.: 10/293,658

(22) Filed: Nov. 12, 2002

(51) Int. Cl.
A61F 2/06 (2006.01)

(52) U.S. Cl. .................................... 623/1.42

(58) Field of Classification Search .............. 623/1.15, 623/1.39–1.46, 1.23, 1.13
See application file for complete search history.

(56) References Cited

U.S. PATENT DOCUMENTS

| | | | |
|---|---|---|---|
| 2,072,303 A | 3/1937 | Herrmann et al. | 128/335.5 |
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,931,287 A | 6/1990 | Bae et al. | 424/484 |
| 4,977,901 A | 12/1990 | Ofstead | 128/772 |
| 4,994,560 A | 2/1991 | Kruper, Jr. et al. | 534/10 |
| 5,040,548 A | 8/1991 | Yock | 128/898 |
| 5,051,978 A * | 9/1991 | Mayer et al. | 369/275.5 |
| 5,059,166 A | 10/1991 | Fischell et al. | 600/3 |
| 5,064,435 A | 11/1991 | Porter | 623/12 |
| 5,087,244 A | 2/1992 | Wolinsky et al. | 604/53 |
| 5,100,429 A | 3/1992 | Sinofsky et al. | 606/195 |
| 5,213,561 A | 5/1993 | Weinstein et al. | 600/7 |
| 5,229,172 A | 7/1993 | Cahalan et al. | 427/536 |
| 5,232,444 A | 8/1993 | Just et al. | 604/96 |
| 5,258,419 A | 11/1993 | Rolando et al. | 522/109 |
| 5,278,200 A | 1/1994 | Coury et al. | 523/112 |
| 5,308,641 A | 5/1994 | Cahalan et al. | 427/2 |
| 5,328,471 A | 7/1994 | Slepian | 604/101 |
| 5,336,518 A | 8/1994 | Narayanan et al. | 623/1 |
| 5,342,283 A | 8/1994 | Good | 600/8 |
| 5,342,621 A | 8/1994 | Eury | 424/423 |
| 5,344,455 A | 9/1994 | Keogh et al. | 623/11 |
| 5,350,800 A | 9/1994 | Verhoeven et al. | 525/54.2 |
| 5,366,504 A | 11/1994 | Andersen et al. | 623/11 |
| 5,411,466 A | 5/1995 | Hess | 600/3 |
| 5,415,938 A | 5/1995 | Cahalan et al. | 428/409 |
| 5,429,618 A | 7/1995 | Keogh | 604/266 |
| 5,443,496 A | 8/1995 | Schwartz et al. | 623/1 |
| 5,464,450 A | 11/1995 | Buscemi et al. | 623/6 |

(Continued)

FOREIGN PATENT DOCUMENTS

DE 19916086 10/1999

(Continued)

OTHER PUBLICATIONS

Fischell et al., "*Low-Dose, β-Particle Emission from 'Stent' Wire Results in Complete, Localized Inhibition of Smooth Muscle Cell Proliferation*", Circulation, vol. 90(6):2956-2963, Dec. 1994.

(Continued)

*Primary Examiner*—Alvin J. Stewart
(74) *Attorney, Agent, or Firm*—Squire, Sanders & Dempsey L.L.P.

(57) ABSTRACT

Coatings for stents that include a polymer and a drug are provided. A method of forming the coatings is also provided.

10 Claims, 6 Drawing Sheets

U.S. PATENT DOCUMENTS

| | | | |
|---|---|---|---|
| 5,464,650 A | 11/1995 | Berg et al. | 427/2.3 |
| 5,470,313 A | 11/1995 | Crocker et al. | 604/96 |
| 5,476,509 A | 12/1995 | Keogh et al. | 623/1 |
| 5,500,013 A | 3/1996 | Buscemi et al. | 623/1 |
| 5,551,954 A | 9/1996 | Buscemi et al. | 623/1 |
| 5,554,182 A | 9/1996 | Dinh et al. | 623/1 |
| 5,571,166 A | 11/1996 | Dinh et al. | 623/1 |
| 5,578,073 A | 11/1996 | Haimovich et al. | 623/1 |
| 5,591,224 A | 1/1997 | Schwartz et al. | 623/1 |
| 5,591,227 A | 1/1997 | Dinh et al. | 623/1 |
| 5,599,352 A | 2/1997 | Dinh et al. | 623/1 |
| 5,605,696 A | 2/1997 | Eury et al. | 424/423 |
| 5,624,411 A | 4/1997 | Tuch | 604/265 |
| 5,628,730 A | 5/1997 | Shapland et al. | 604/21 |
| 5,628,785 A | 5/1997 | Schwartz et al. | 623/1 |
| 5,637,113 A | 6/1997 | Tartaglia et al. | 623/1 |
| 5,649,977 A | 7/1997 | Campbell | 623/1 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,693,085 A | 12/1997 | Buirge et al. | 623/1 |
| 5,693,376 A | 12/1997 | Fetherston et al. | 427/523 |
| 5,697,967 A | 12/1997 | Dinh et al. | 623/1 |
| 5,700,286 A | 12/1997 | Tartaglia et al. | 623/1 |
| 5,702,818 A | 12/1997 | Cahalan et al. | 428/109 |
| 5,707,385 A | 1/1998 | Williams | 606/192 |
| 5,711,812 A | 1/1998 | Chapek et al. | 118/723 |
| 5,713,949 A | 2/1998 | Jayaraman | 623/1 |
| 5,716,981 A | 2/1998 | Hunter et al. | 514/449 |
| 5,722,984 A | 3/1998 | Fischell et al. | 606/198 |
| 5,730,698 A | 3/1998 | Fischell et al. | 600/3 |
| 5,766,710 A | 6/1998 | Turnlund et al. | 428/36.1 |
| 5,769,883 A | 6/1998 | Buscemi et al. | 623/1 |
| 5,769,884 A | 6/1998 | Solovay | 623/1 |
| 5,782,742 A | 7/1998 | Crocker et al. | 600/3 |
| 5,800,392 A | 9/1998 | Racchini | 604/96 |
| 5,811,151 A | 9/1998 | Hendriks et al. | 427/2.24 |
| 5,824,048 A | 10/1998 | Tuch | 623/1 |
| 5,824,049 A | 10/1998 | Ragheb et al. | 623/1 |
| 5,826,586 A | 10/1998 | Mishra et al. | 128/898 |
| 5,830,178 A | 11/1998 | Jones et al. | 604/49 |
| 5,837,313 A | 11/1998 | Ding et al. | 427/2.21 |
| 5,840,009 A * | 11/1998 | Fischell et al. | 600/3 |
| 5,843,172 A | 12/1998 | Yan | 623/1 |
| 5,851,231 A * | 12/1998 | Wolff et al. | 623/1.42 |
| 5,851,508 A | 12/1998 | Greff et al. | 424/9.411 |
| 5,857,998 A | 1/1999 | Barry | 604/96 |
| 5,858,556 A | 1/1999 | Eckhart et al. | 428/586 |
| 5,858,990 A | 1/1999 | Walsh | 514/44 |
| 5,865,814 A | 2/1999 | Tuch | 604/265 |
| 5,866,113 A | 2/1999 | Hendriks et al. | 424/78.17 |
| 5,871,437 A | 2/1999 | Alt | 600/3 |
| 5,873,904 A | 2/1999 | Ragheb et al. | 623/1 |
| 5,893,840 A | 4/1999 | Hull et al. | 604/96 |
| 5,897,911 A | 4/1999 | Loeffler | 427/2.25 |
| 5,902,631 A | 5/1999 | Wang et al. | 427/2.1 |
| 5,916,234 A | 6/1999 | Lam | 606/198 |
| 5,925,552 A | 7/1999 | Keogh et al. | 435/174 |
| 5,928,916 A | 7/1999 | Keogh | 435/174 |
| 5,968,091 A | 10/1999 | Pinchuk et al. | 623/1 |
| 5,968,092 A * | 10/1999 | Buscemi et al. | 128/898 |
| 5,971,954 A | 10/1999 | Conway et al. | 604/96 |
| 5,972,027 A * | 10/1999 | Johnson | 623/1.42 |
| 5,972,029 A | 10/1999 | Fuisz | 623/1 |
| 5,980,564 A | 11/1999 | Stinson | 623/1 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,013,099 A | 1/2000 | Dinh et al. | 623/1 |
| 6,015,541 A | 1/2000 | Greff et al. | 424/1.25 |
| 6,019,789 A | 2/2000 | Dinh et al. | 623/1 |
| 6,024,918 A | 2/2000 | Hendriks et al. | 422/44 |
| 6,033,719 A | 3/2000 | Keogh | 427/2.12 |
| 6,042,606 A | 3/2000 | Frantzen | 623/1 |
| 6,042,875 A | 3/2000 | Ding et al. | 427/2.24 |
| 6,071,305 A | 6/2000 | Brown et al. | 623/1 |
| 6,080,190 A | 6/2000 | Schwartz | 623/1 |
| 6,093,199 A | 7/2000 | Brown et al. | 606/200 |
| 6,096,070 A | 8/2000 | Ragheb et al. | 623/1 |
| 6,099,455 A | 8/2000 | Columbo et al. | 600/3 |
| 6,099,559 A | 8/2000 | Nolting | 623/1.16 |
| 6,099,561 A | 8/2000 | Alt | 623/1.44 |
| 6,106,454 A | 8/2000 | Berg et al. | 600/3 |
| 6,110,483 A | 8/2000 | Whitbourne et al. | 424/423 |
| 6,140,127 A | 10/2000 | Sprague | 435/395 |
| 6,140,431 A | 10/2000 | Kinker et al. | 526/79 |
| 6,153,252 A | 11/2000 | Hossainy et al. | 427/2.3 |
| 6,165,212 A | 12/2000 | Dereume et al. | 623/1.13 |
| 6,168,619 B1 | 1/2001 | Dinh et al. | 623/1.13 |
| 6,203,551 B1 | 3/2001 | Wu | 606/108 |
| 6,214,901 B1 | 4/2001 | Chudzik et al. | 523/113 |
| 6,224,894 B1 | 5/2001 | Jamiolkowski et al. | 424/426 |
| 6,231,590 B1 | 5/2001 | Slaikeu et al. | 606/200 |
| 6,242,041 B1 | 6/2001 | Katoot et al. | 427/2.24 |
| 6,253,443 B1 | 7/2001 | Johnson | 29/557 |
| 6,254,632 B1 * | 7/2001 | Wu et al. | 623/1.15 |
| 6,258,121 B1 | 7/2001 | Yang et al. | 623/1.46 |
| 6,262,034 B1 | 7/2001 | Mathiowitz et al. | 514/44 |
| 6,273,913 B1 | 8/2001 | Wright et al. | 623/1.42 |
| 6,287,628 B1 * | 9/2001 | Hossainy et al. | 427/2.3 |
| 6,319,520 B1 | 11/2001 | Wuthrich et al. | 424/482 |
| 6,344,035 B1 | 2/2002 | Chudzik et al. | 604/265 |
| 6,379,379 B1 | 4/2002 | Wang | 623/1.31 |
| 6,379,381 B1 | 4/2002 | Hossainy et al. | 623/1.42 |
| 6,395,326 B1 * | 5/2002 | Castro et al. | 427/2.24 |
| 6,413,272 B1 | 7/2002 | Igaki | 623/1.15 |
| 6,488,701 B1 * | 12/2002 | Nolting et al. | 623/1.13 |
| 6,558,733 B1 * | 5/2003 | Hossainy et al. | 427/2.24 |
| 6,596,296 B1 * | 7/2003 | Nelson et al. | 424/426 |
| 6,663,662 B2 * | 12/2003 | Pacetti et al. | 623/1.13 |
| 6,699,281 B2 * | 3/2004 | Vallana et al. | 623/1.42 |
| 6,702,849 B1 * | 3/2004 | Dutta et al. | 623/1.42 |
| 6,712,845 B2 * | 3/2004 | Hossainy | 623/1.42 |
| 6,716,444 B1 * | 4/2004 | Castro et al. | 424/422 |
| 6,764,505 B1 * | 7/2004 | Hossainy et al. | 623/1.15 |
| 6,783,543 B2 * | 8/2004 | Jang | 623/1.15 |
| 6,790,228 B2 * | 9/2004 | Hossainy et al. | 623/1.46 |
| 6,805,709 B1 * | 10/2004 | Schaldach et al. | 623/1.46 |
| 6,849,089 B2 * | 2/2005 | Stoll | 623/1.42 |
| 6,939,376 B2 * | 9/2005 | Shulze et al. | 623/1.42 |
| 7,056,338 B2 * | 6/2006 | Shanley et al. | 623/1.42 |
| 7,083,642 B2 * | 8/2006 | Sirhan et al. | 623/1.42 |
| 2001/0001806 A1 | 5/2001 | Turnlund et al. | 600/3 |
| 2002/0068969 A1 | 6/2002 | Shanley et al. | 623/1.16 |
| 2002/0183581 A1 | 12/2002 | Yoe et al. | 600/3 |
| 2003/0068355 A1 * | 4/2003 | Shanley et al. | 424/426 |
| 2003/0073961 A1 * | 4/2003 | Happ | 604/274 |
| 2003/0104028 A1 * | 6/2003 | Hossainy et al. | 424/424 |
| 2003/0181973 A1 * | 9/2003 | Sahota | 623/1.15 |
| 2004/0086493 A1 * | 5/2004 | Hubbell et al. | 424/93.7 |
| 2004/0098106 A1 * | 5/2004 | Williams et al. | 623/1.15 |
| 2004/0106987 A1 * | 6/2004 | Palasis et al. | 623/1.42 |
| 2004/0122506 A1 * | 6/2004 | Shanley et al. | 623/1.16 |
| 2004/0127976 A1 * | 7/2004 | Diaz | 623/1.42 |
| 2004/0162609 A1 * | 8/2004 | Hossainy et al. | 623/1.42 |
| 2005/0033412 A1 * | 2/2005 | Wu et al. | 623/1.15 |
| 2005/0107864 A1 * | 5/2005 | Hong et al. | 623/1.15 |
| 2005/0161859 A1 * | 7/2005 | Miller et al. | 264/209.1 |
| 2006/0122697 A1 * | 6/2006 | Shanley et al. | 623/1.42 |

| | | |
|---|---|---|
| 2006/0129225 A1 * | 6/2006 | Kopia et al. ............... 623/1.13 |

FOREIGN PATENT DOCUMENTS

| | | |
|---|---|---|
| EP | 0 627 226 | 12/1994 |
| EP | 0 665 023 | 8/1995 |
| EP | 0 701 803 | 3/1996 |
| EP | 0 850 604 | 7/1998 |
| EP | 0 970 711 | 1/2000 |
| EP | 0 972 498 | 1/2000 |
| EP | 0 850 651 | 6/2000 |
| EP | 1 103 234 | 5/2001 |
| WO | WO 90/01969 | 3/1990 |
| WO | WO 91/12846 | 9/1991 |
| WO | WO 97/45105 | 12/1997 |
| WO | WO 98/23228 | 6/1998 |
| WO | WO 99/63981 | 12/1999 |
| WO | WO 00/12147 | 3/2000 |
| WO | WO 00/64506 | 11/2000 |
| WO | WO 01/01890 | 1/2001 |
| WO | WO 01/45763 | 6/2001 |
| WO | WO 01/91918 | 12/2001 |
| WO | WO 02/47731 | 6/2002 |
| WO | WO2004/000379 A1 * | 12/2003 |

OTHER PUBLICATIONS

Hehrlein et al., "Low-Dose Radioactive Endovascular Stents Prevent Smooth Muscle Cell Proliferation and Neointimal Hyperplasia in Rabbits", Circulation, vol. 92(6):1570-1575, Sep. 15, 1995.

Liermann et al., "Prophylactic Endovascular Radiotherapy to Prevent Intimal Hyperplasia after Stent Implantation in Femoropopliteal Arteries", CardioVascular and Interventional Radiology 17:12-16, 1994.

U.S. Appl. No. 09/697,106, filed Oct. 26, 2000, Hossainy et al.
U.S. Appl. No. 09/834,012, filed Apr. 12, 2001, Hossainy et al.
U.S. Appl. No. 09/872,135, filed May 31, 2001, Yoe et al.
U.S. Appl. No. 09/894,293, filed Jun. 27, 2001, Roorda et al.
U.S. Appl. No. 09/885,753, filed Jun. 29, 2001, Hossainy et al.
U.S. Appl. No. 10/177,154, filed Jun. 21, 2002, Hossainy et al.

Barath et al., Low Dose of Antitumor Agents Prevents Smooth Muscle Cell Proliferation After Endothelial Injury, JACC 13(2):252A (1989) (Abstract).

Malik et al., Development of an Energetic Ion Assisted Mixing and Deposition Process for $TIN_x$ and Diamondlike Carbon Films, Using a Co-axial Geometry in Plasma Source Ion Implantation, J. Vac. Sci. Technol. A 15(6):2875-2879 (Nov./Dec. 1997).

Malik et al., Overview of Plasma Source Ion Implantation Research at University of Wisconsin-Madison, J. Vac. Sci. Technol. B 12(2):843-849 (Mar./Apr. 1994).

Malik et al., Sheath Dynamics and Dose Analysis for Planar Targets in Plasma Source Ion Implantation, Plasma Sources Sci. Technol. 2:81-85 (1993).

Matsumaru et al., Embolic Materials for Endovascular Treatment of Cerebral Lesions, J. Biomater. Sci. Polymer Edn. 8(7):555-569 (1997).

Miyazaki et al., Antitumor Effect of Implanted Ethylene-Vinyl Alcohol Copolymer Matrices Containing Anticancer Agents on Ehrlich Ascites Carcinoma and P388 Leukemia in Mice, Chem. Pharm. Bull. 33(6):2490-2498 (1985).

Miyazawa et al., Effects of Pemirolast and Tranilast on Intimal Thickening After Arterial Injury in the Rat, J. Cardiovasc. Pharmacol. 30(2):157-162 (1997).

Ohsawa et al., Preventive Effects of an Antiallergic Drug, Pemirolast Potassium, on Restenosis After Percutaneous Transluminal Coronary Angioplasty, Am. Heart J. 136(6):1081-1087 (Dec. 1998).

Scheuer et al., Model of Plasma Source Ion Implantation in Planar, Cylindrical, and Spherical Geometries, J. Appl. Phys. 67(3):1241-1245 (Feb. 1990).

Serruys et al., I Like the Candy, I Hate the Wrapper; the $^{32}P$ Radioactive Stent, Circulation 101:3-7 (Jan. 2000).

Shamim et al., Measurement of Electron Emission Due to Energetic Ion Bombardment in Plasma Source Ion Implantation, J. Appl. Phys. 70(9):4756-4759 (Nov. 1991).

Shamim et al., Measurements of Spatial and Temporal Sheath Evolution for Spherical and Cylindrical Geometries in Plasma Source Ion Implantation, J. Appl. Phys. 69(5):2904-2908 (Mar. 1991).

Shigeno, Prevention of Cerebrovascular Spasm by Bosentan, Novel Endothelin Receptor, Chem. Abstracts 125:212307 (1996).

van der Giessen et al., "Edge Effect" of $^{32}P$ Radioactive Stents is Caused by the Combination of Chronic Stent Injury and Radioactive Dose Falloff, Circulation 104:2236-2241 (Oct. 30, 2001).

Wiesendanger et al., Contributions Of Scanning Probe Microscopy And Spectroscopy To The Investigation And Fabrication Of Nanometer-Scale Structures, J. Vac. Sci. Technol. B, 12(2):515-529 (Mar./Apr. 1994).

\* cited by examiner

STENT WITH DRUG COATING

BACKGROUND OF THE INVENTION

1. Field of the Invention

This invention is directed to an implantable device, such as a stent, having a polymeric drug coating, and method of forming the same.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to remodel the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis, an expandable, intraluminal prosthesis, also known as a stent, is implanted in the lumen to maintain the vascular patency.

Stents act as scaffoldings, functioning to physically hold open and, if desired, to expand the wall of the passageway. Typically, stents are capable of being compressed so that they can be inserted through small lumens via catheters and then expanded to a larger diameter once they are at the desired location. Mechanical intervention via stents has reduced the rate of restenosis as compared to balloon angioplasty. Yet, restenosis is still a significant clinical problem with rates ranging from 20–40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a drug at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method of medicating stents involves the use of a polymeric carrier coated onto the surface of the stent. A composition including a solvent, a polymer dissolved in the solvent, and a drug dispersed in the blend is applied to the stent by immersing the stent in the composition or by spraying the composition onto the stent. The solvent is allowed to evaporate, leaving on the stent surfaces a coating of the polymer and the drug impregnated in the polymer.

A potential shortcoming of conventional medicated stents is that there can be an unequal release of the drug to different areas of the treatment site. For instance, in conventional stents, the concentration of the drug on the stent is essentially constant along the length of the stent. In such drug delivery stents, after the stent is implanted in the biological lumen and the drug is released from the polymeric matrix, the concentration of the drug that is applied to the tissues along the length of the stent will not be constant along the length of the stent. In particular, the drug concentration in the blood stream is higher in the distal region of the biological lumen than the proximal region.

Referring to FIG. 1, a stent 10 with a polymeric drug coating is implanted into a biological lumen 12, which has a proximal region 14 and a distal region 16. The blood in biological lumen 12 flows from proximal region 14 to distal region 16 as the drug is released from the polymeric coating. If the quantity and release rate of the drug are constant over the length of stent 10, when stent 10 is first implanted into biological lumen 12, the drug concentration in the blood will be constant along the length of stent 10 as graphically illustrated in FIG. 2A. As shown in FIG. 2B, however, over time more drug is released into the blood stream and the drug concentration in the blood in distal region 16 becomes significantly higher as compared to the drug concentration in proximal region 14. As a result, depending on the biological needs of the tissue in the respective regions, the tissue in distal region 16 can receive too much drug whereas the tissue in proximal region 14 may not receive enough drug.

Another example of a related shortcoming of conventional medicated stents is that there can be an unequal release of the drug to the tissues adjacent to the points of contact between the stent and the tissues. Referring to FIG. 1, stent 10 can have a tubular body of structural members including struts 18 and connecting elements 20 that form a network structure. Struts 18 are radially expandable and interconnected by connecting elements 20 that are disposed between adjacent struts 18. Both struts 18 and connecting elements 20 have an outer (or lumen contacting) surface and an inner surface.

In conventional stents, the concentration of drugs on the stent is essentially constant along the length of struts 18 and connecting elements 20, including any curved or bent segments. Referring to FIG. 3, when stent 10 is inserted into a biological lumen, stent 10 forms multiple contact points 30 with the tissue as shown with lines A—A and B—B. As the drug in the polymer is released from multiple contact points 30 to the tissue, delivery zones 32 are formed. If the quantity of the drug is the same along lines A—A and B—B, then some of delivery zones 32, for example delivery zone 32A, overlap. As a result, the tissue area adjacent to the overlapping delivery zones receives a greater quantity of drug than other tissue areas. Therefore, some tissue adjacent to contact points 30 may receive too much drug.

Accordingly, what is needed is a coating for a stent that addresses the aforementioned drawbacks.

SUMMARY OF THE INVENTION

In accordance with one aspect of the invention, a stent is disclosed including a body having a first end and a second end and carrying a coating containing a drug. The concentration of the drug in the coating increases along the length of the body of the stent from the first end to the second end.

In accordance with another aspect of the invention, a stent is disclosed including a body with a first end and a second end and carrying a coating containing a drug. The release rate of the drug from the coating increases along the length of the body from the first end to the second end.

In a further aspect, a stent is disclosed that includes a body having a coating carrying a drug, where the concentration of the drug in the coating increases along at least a circumference of the body of the stent.

In accordance with yet aspect of the invention, a strut for a radially expandable stent is disclosed having generally linear segments interrupted by a curved or bent segment. The strut also has a coating containing a drug disposed on the strut, where the concentration of the drug in the coating is greater in at least a portion of the curved or bent segment as compared to the linear segments.

In another aspect, a method of coating a stent is disclosed, the stent having a first end and a second end. The method includes applying a composition including a drug and a polymer to the stent, where the amount of drug applied to the stent gradually increases along the length of the stent from the first end to the second end.

DETAILED DESCRIPTION

Variable Drug Concentration or Release Rate Along the Length of the Stent

Figure 1:
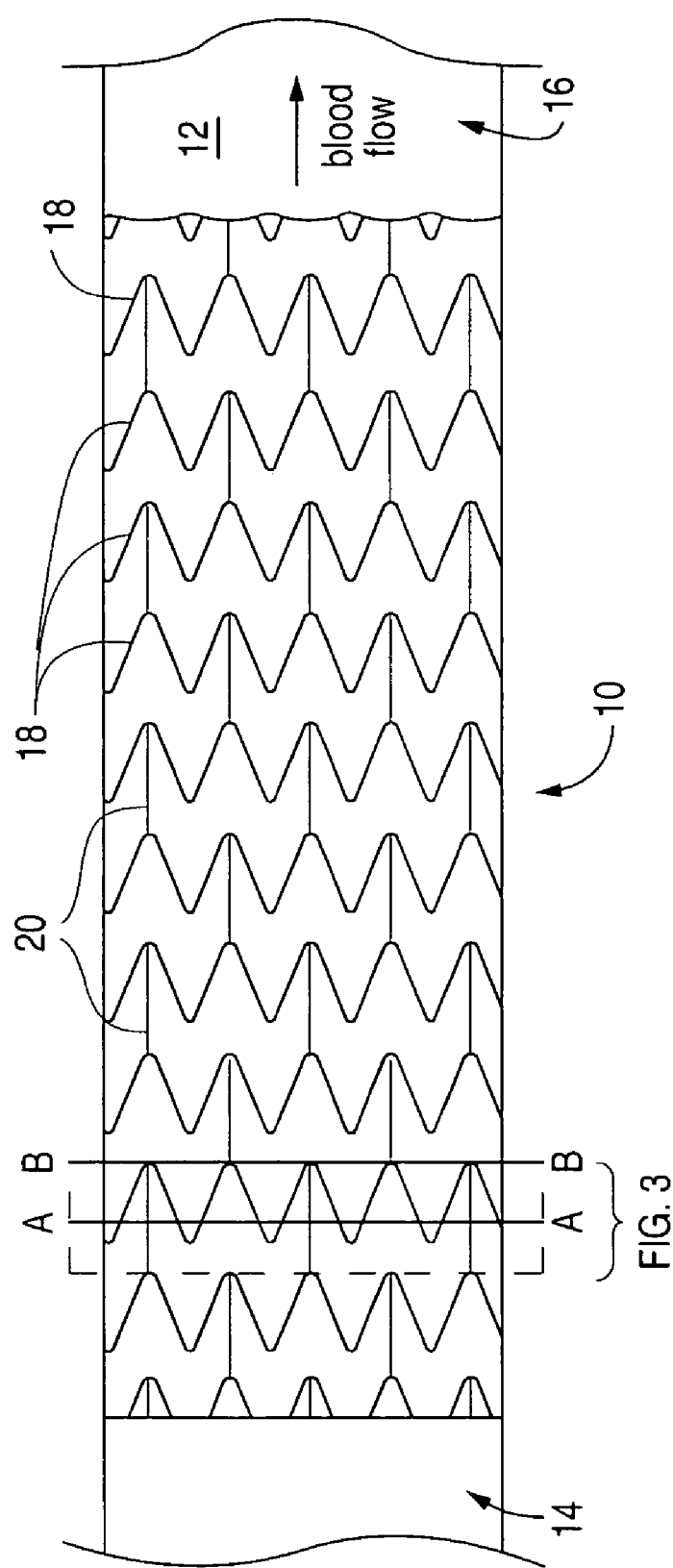
FIG. 1 is a side view of a conventional stent inserted into a biological lumen.
Figure 2A:
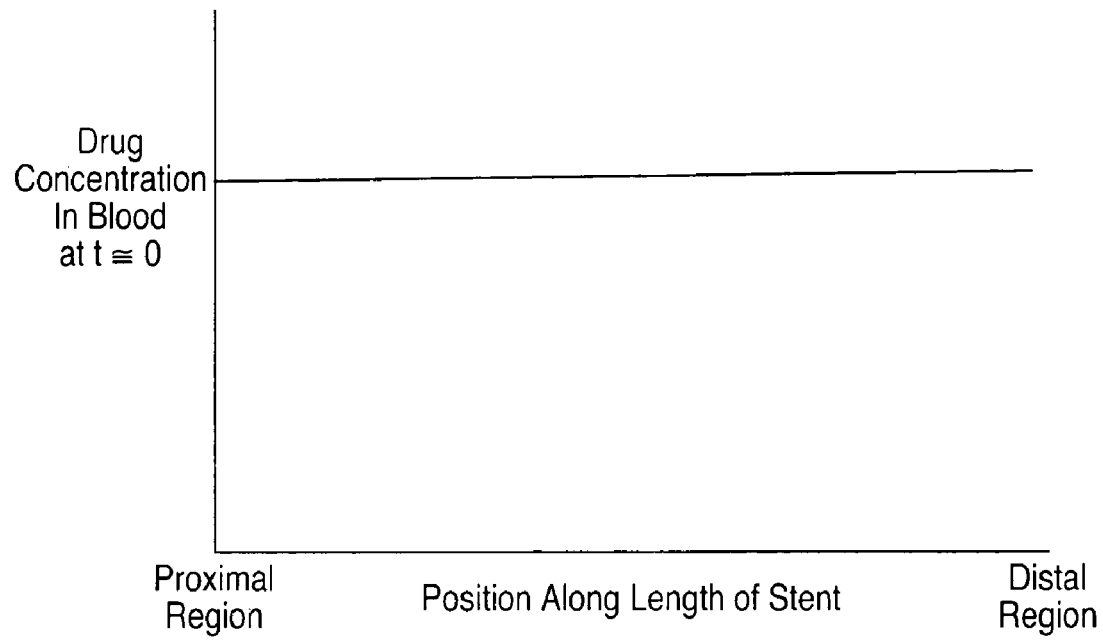
FIGS. 2A and 2B are graphs of drug concentrations in blood along the length of the stent illustrated in FIG. 1.
Figure 2B:
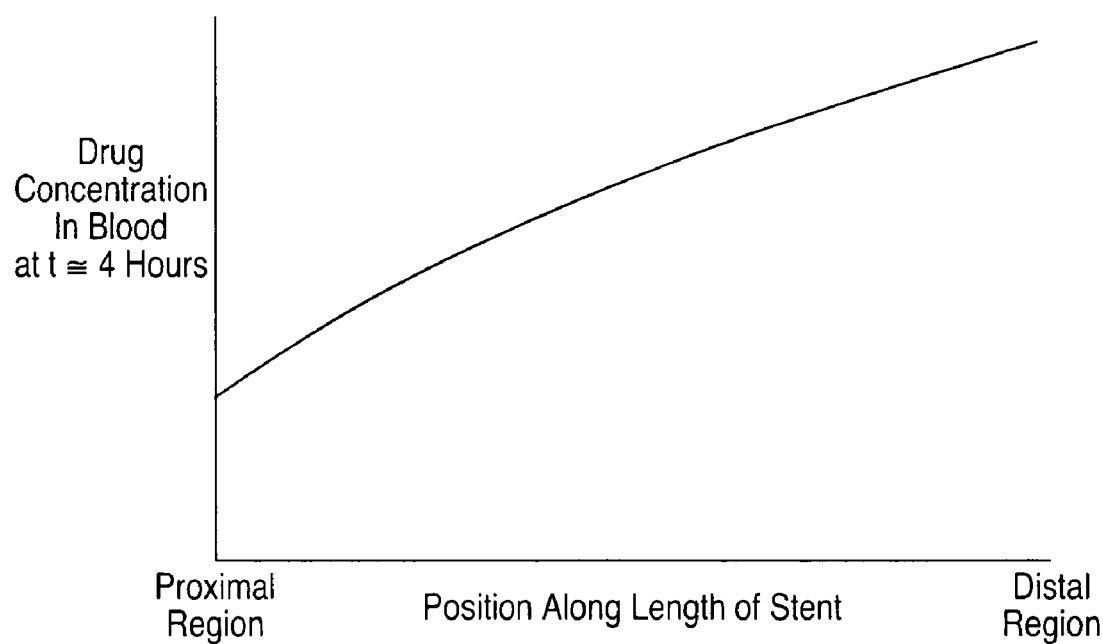
Figure 3:
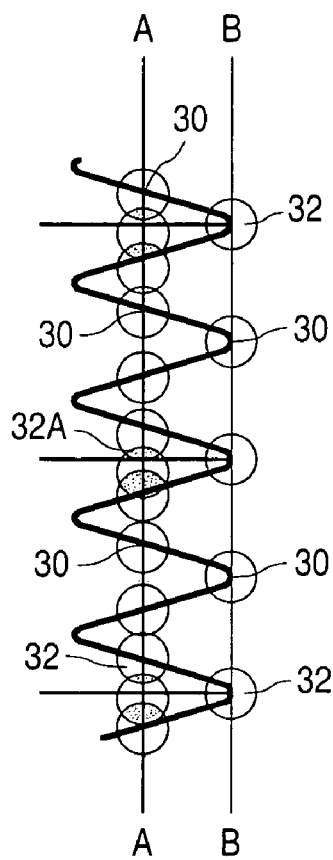
FIG. 3 is an enlarged view of a portion of the stent illustrated in FIG. 1.
Figure 5:
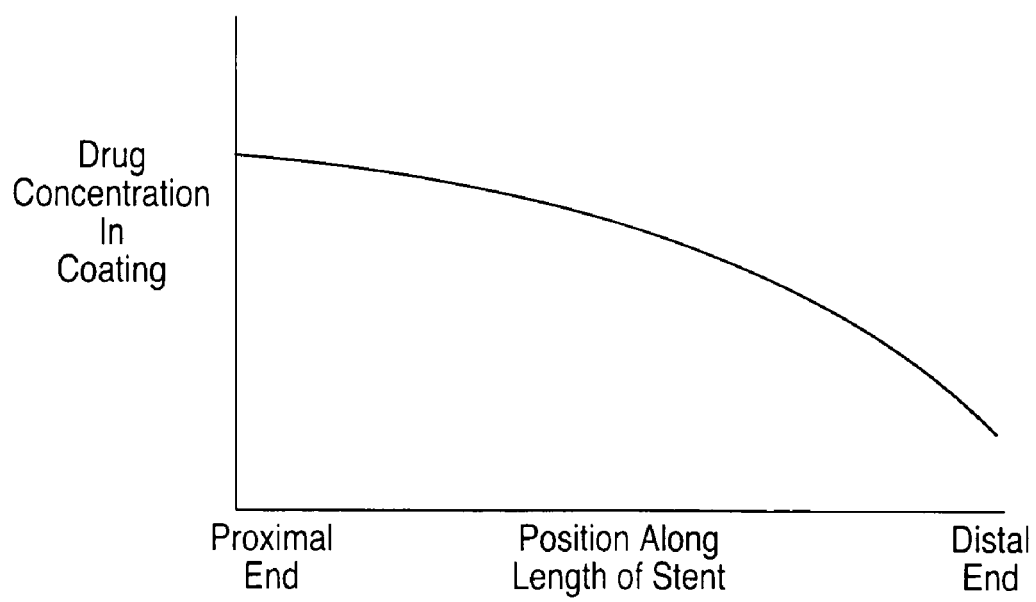
FIG. 5 is a graph of the drug concentration in a stent coating along the length of the stent in accordance with one embodiment of the invention.
Figure 4:
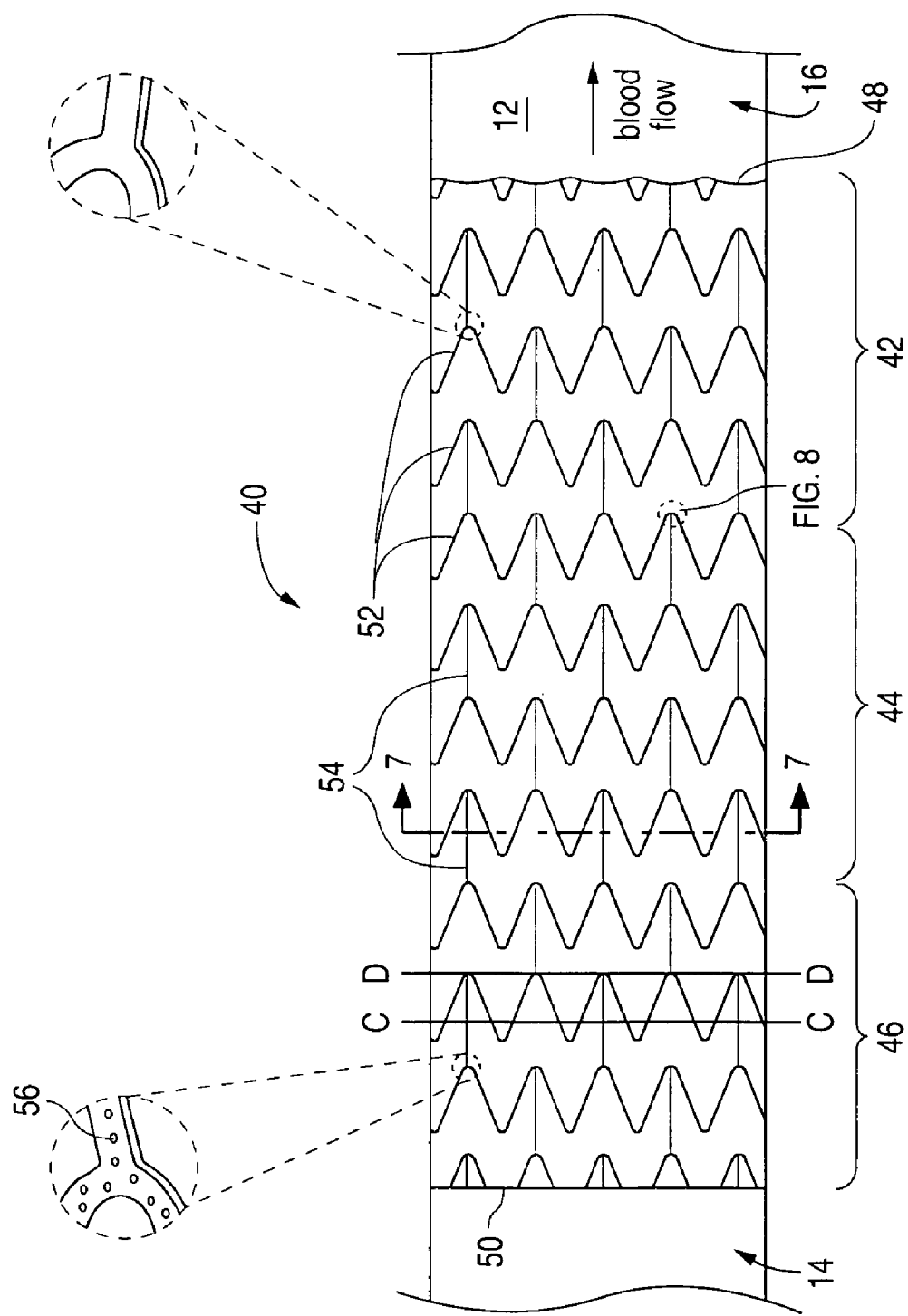
FIG. 4 is a side view of one embodiment of a stent of the present invention inserted into a biological lumen.

The present invention is directed to a stent with a polymeric drug coating having a variable drug concentration or release rate along the length of the stent. Referring to FIG. 4, for example, a stent 40 coated with a polymeric drug coating can have a first segment 42, a second segment 44 and a third segment 46 along the length of stent 40, disposed between a first end 48 and a second end 50. In an embodiment of the present invention, the drug concentration in the coating gradually or incrementally increases along the length of stent 40 from first end 48 to second end 50. FIG. 5, for example, graphically illustrates a drug concentration in a coating that gradually increases along the length of a stent from the distal end of stent 40 to the proximal end of stent 40. The increase of the drug concentration can also be graphically illustrated to be linear or step-wise/incremental. In another embodiment of the present invention, the release rate of the drug from the coating gradually or incrementally increases along the length of stent 40 from first end 48 to second end 50.

By varying the drug concentration in the polymeric coating, or the release rate of the drug from the polymeric coating, the present invention advantageously provides a coating that provides uniform drug delivery to the target site along the length of stent 40. The distribution of the drug in the blood stream along the length of the stented portion of the biological lumen depends on the Peclet number which is defined as $$Pe = \frac{VL}{D}$$

where V is the velocity of the blood stream, L is the length of the stented portion of the lumen, and D is the diffusivity of the drug in the blood stream. In essence, the Peclet number is the ratio of the convection to diffusion. As can be understood by the above equation, if the velocity of the blood stream is relatively high in comparison to the diffusivity, then much of the drug released from the stent will be carried away by the blood flow from the treatment area adjacent to the stent. However, in a typical blood vessel, the Peclet number is relatively low and diffusion dominated. As a result, the drug released from the stent will remain present in the blood stream at the local treatment site and will be available for absorption by the arterial wall. This is especially advantageous for portions of the arterial walls that are not being contacted by the stent but are being contacted by the blood. However, the relatively low Peclet number in a typical blood vessel results in a higher concentration of the drug in the blood stream in the distal region of the biological lumen as compared to the proximal region if the drug concentration is uniform along the length of the stent.

Figure 6A:
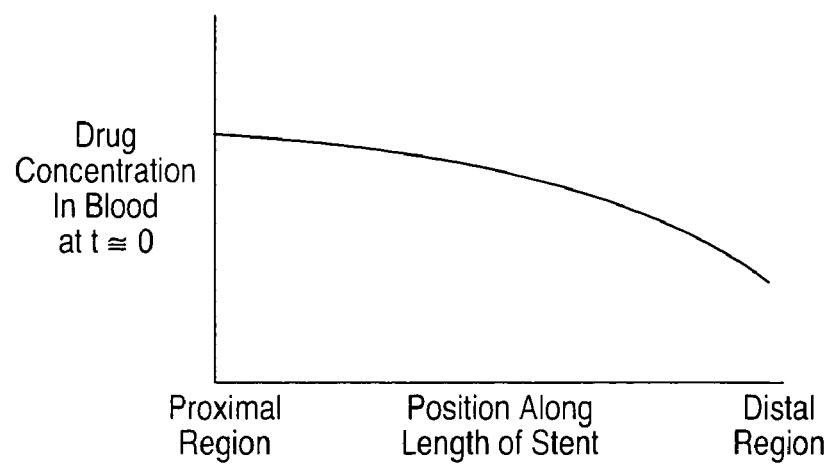
FIGS. 6A and 6B are graphs of drug concentrations in blood along the length of the stent illustrated in FIG. 4.
Figure 6B:
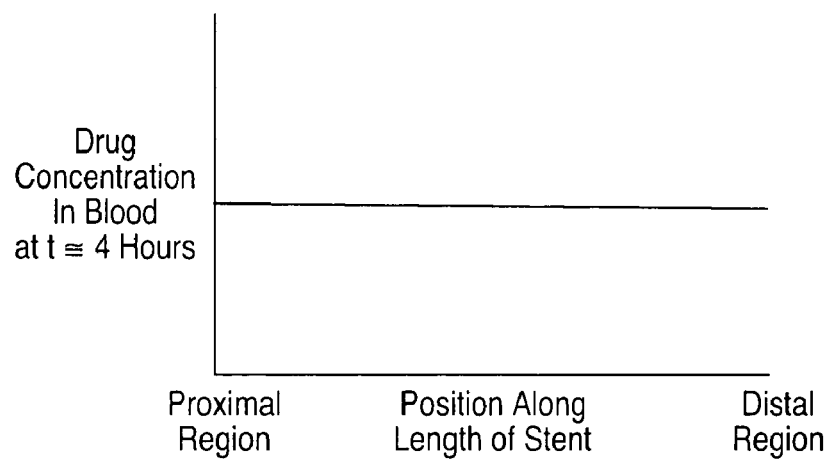

A stent coated in accordance with the various embodiments of the present invention can provide a drug concentration in the blood that is initially high in the proximal region of lumen 12, as graphically illustrated in FIG. 6A. However, as shown in FIG. 6B, over time more drug is released into the blood stream and the drug concentration in the blood becomes uniformly distributed along the length of stent 40, providing for a beneficial long-term treatment regime.

Variable Drug Concentration or Release Rate Along the Circumference of the Stent The present invention is also directed to a stent with a polymeric drug coating having a variable drug concentration or release rate along the circumference of the stent. A stent with such a coating can be particularly suitable to use when it is known that one side of a lumen is in greater need of a drug than the other side. The coating can be customized so that a targeted dose of the drug or a particular drug is delivered to one side of the lumen.

Figure 7:
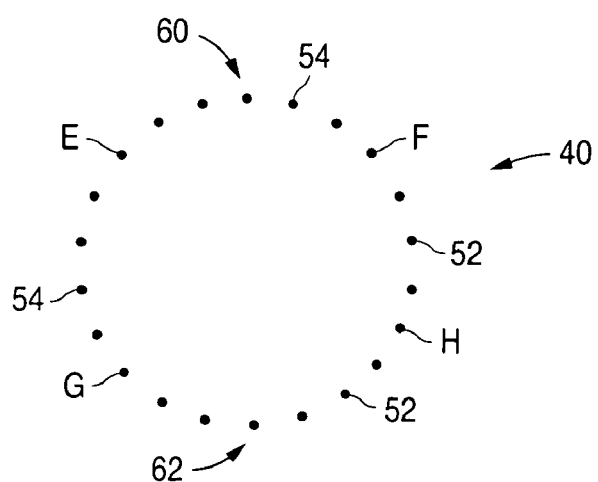
FIG. 7 is a cross-section along line 7—7 in FIG. 4.

The stent of the present invention, for instance, can have any suitable number of coating segments along the radial perimeter of the stent, where the concentration of the drug in the coating is higher along selected segments as compared to other segments. FIG. 7 illustrates the radial perimeter of a stent with two coating segments. A first coating segment 60 extends from point E to point F, and a second coating segment 62 extends from point G to point H. In an embodiment, the drug concentration of the coating along first segment 60 can be greater than the drug concentration of the coating along second segment 62. In another embodiment, the release rate of the drug from the coating is greater in first segment 60 as compared to second segment 62.

In another embodiment, the concentration of the drug in the coating gradually increases along at least a portion of the radial perimeter of the stent. For example, referring to FIG. 7, the concentration of the drug can gradually increase from point E to point G and from point F to point H. Also, in an embodiment, the release rate of the drug from the coating can gradually increase along at least a portion of the radial perimeter of the stent.

Variable Drug Concentration or Release Rate Along Struts of the Stent

Figure 8:
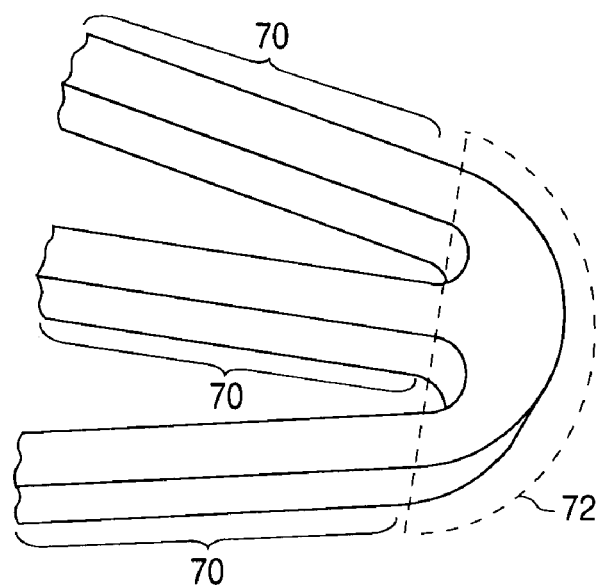
FIGS. 8 and 9 are an enlarged views of a portion of the stent illustrated in FIG. 4 in accordance with embodiments of the invention.

The present invention is further directed to a stent with a polymeric drug coating having a variable drug concentration or release rate along the length of individual structural members of stent 40 such as struts 52 and connecting members 54. In this way, the drug concentration or release rate on the individual structural members can be tailored to match the geometrical configuration of the stent structure. In other words, the coating can have a variable drug concentration or release rate along the length of individual structural members to account for how the structural members are positioned relative to one another in the stent structure, e.g., as deployed in the expanded state. Referring to FIG. 8, for instance, individual strut 52 or connecting member 54 can have generally linear segments 70 that are interrupted by a curved or bent segment 72. In an embodiment, the concentration of the drug is greater in at least a portion of curved segment 72 as compared to linear segments 70. In another embodiment, the concentration of the drug is greatest at the vertex of curved segment 72 of strut 52.

Figure 9:
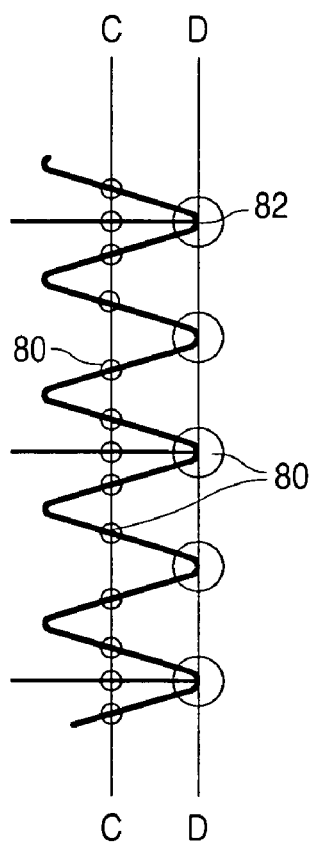

By coating a stent with a coating having a variable drug concentration or release rate along the length of individual struts or connecting elements of the stent, a stent can carry a drug with delivery zones of different sizes for delivery of the drug to a selected portion of a biological lumen of a patient. "Delivery zones" refers to the region of the treatment site in which the drug is delivered, for example, by diffusion. After a stent coated in accordance with the present invention is inserted into a biological lumen of a patient, the delivery zones will not significantly overlap. Referring to FIG. 9, if the concentration of the drug is lower along the line C—C than D—D, as the drug in the polymer is released, delivery zones 80 formed around contact points 82 do not significantly overlap. As a result, the tissue area adjacent to delivery zones 80 receives a more uniform amount of drug.

Methods of Varying Drug Concentration

The drug concentration on the stent can be varied by using different approaches. For ease of discussion, the following describes how to vary the drug concentration along the length of the stent. However, one of ordinary skill in the art will understand that these same approaches can also be used to vary the drug concentration along the circumference of the stent or along individual structural members such as the struts.

In one embodiment, struts 52 and connecting elements 54 can have depots 56 for containing a drug. By varying the number of depots along the length of stent 40, the drug concentration can be varied along the length of stent 40. For instance, as shown in the enlarged windows of FIG. 4, struts 52 and connecting elements 54 in third segment 46 can contain the most number of depots 56, whereas struts 52 and connecting elements 54 located in first segment 42 contain the least. Alternatively, depots 56 of third segment 46 can be formed to contain the largest volume of the drug and depots 56 of first segment 42 can be formed to contain the smallest volume of drug. The volume of depot 56 can be increased by increasing the depth and/or diameter of depot 56.

Depots 56 may have a depth of about one half of the thickness of struts 52 or connecting elements 54 at the location of depots 56. For example, depots 56 can have a depth of about 60–80 microns. Depots can take various shapes, with representative shapes including a truncated cone shape or a dimple shape.

Depots can be formed using any suitable etching technique known to one having ordinary skill in the art such as chemical etching. Chemical etching is a manufacturing technique whereby selected portions of a metal surface are blanked or dissolved away using a chemical etchant or an acid. The desired placement of depots 56 can be performed by physically protecting portions of the stent material. Another representative example of a method of forming depots 56 includes using lasers, such as excimer lasers and Nd:YAG (neodymium yttrium aluminum garnet) lasers.

In another embodiment, the drug concentration on the stents can be varied by modifying the surface of the stents in order to increase the surface area of the stents. In other words, the surface area of the stents can be roughened to provide an irregular surface area and when the polymeric drug coating is applied, the drug concentration varies along the length of the stent because more coating can be applied to the portions of the stent which have a greater surface area than the other portions of the stent. In one embodiment, the roughness factor ($h_r$) gradually or incrementally changes along the entire length of stent 40.

For instance, for a length of strut 52 or connecting element 54, a surface area ($\gamma$) is provided which is given by the equation: $\gamma = 2\pi r l h_r$, where r is a radius (r) of strut 52 or connecting element 54, l is a length (l) of the segment of strut 52 or connecting element 54, and $h_r$ is the roughness factor ($h_r$) (i.e., degree of roughness) of the segment. If the surface is entirely smooth, the roughness factor ($h_r$) is 1.0. However, if the surface area is roughened, then the roughness factor ($h_r$) is greater than 1.0. If surface area ($\gamma$) varies throughout a given length (l) then the drug concentration will vary throughout that same length (l). Given the equation $\gamma = 2\pi r l h_r$, it can be seen that if the variable $h_r$ of the equation fluctuates in value for the same given length (l), then so too will the surface area ($\gamma$) of strut 52 or connecting element 54 within the given length (l). A change in the surface area along a given length (l) is given by the equation: $\gamma' = 2\pi r l \Delta h_r$. The drug concentration deliverable to biological vessel 12 is increased in corresponding portions of strut 52 or connecting element 54 where ($h_r$) is greater than 1.0.

Various methods can be used to increase the roughness factor ($h_r$). Representative examples include chemical, plasma, laser, mechanical or other methods of etching. For example, stent 40 can be dry etched by sand blasting or plasma etched with argon in order to increase roughness. The roughness factor ($h_r$) on struts or connecting elements can also be increased by a lithography technique. For example, a composition including a polymer (e.g., ethylene vinyl alcohol copolymer) dissolved in a solvent can be applied to a stent. The solvent can then be essentially removed to form a polymeric coating. The stent can then be selectively treated with a solvent, such as dimethyl sulfoxide (DMSO), dimethyl formamide (DMF), or dimethyl acetamide (DMAC) to remove portions of the polymer coating.

In another embodiment, the drug concentration can be varied by providing a stent with variable structural dimensions so that the surface area of the struts and connecting elements is variable. For example, the radius or thickness of struts 52 and connecting elements 54 can be varied along the length of stent 40 to provide a variable surface area. In one embodiment, a surface area ($\gamma$) gradually or incrementally increases along the entire length of stent 40. The drug concentration, therefore, can gradually or incrementally increase along the entire length of stent 40. Given the equation $\gamma=2\pi r l h_r$, it can be seen that if the variable r of the equation fluctuates in value for the same given length (l), then so too will the surface area ($\gamma$) of strut 52 or connecting element 54 within the given length (l). A change in the surface area along a given length (l) is given by the equation: $\gamma''=2\pi\Delta r l h_r$.

Stent 40 can be manufactured by using a laser to cut from, for example, a stainless steel tube. The laser cutting process can be run according to an automated process to form a particular stent configuration. For example, in order to increase radius (r) in particular struts 52 and connecting elements 54, the automated process is programmed to cut with an increasing radius (r) along the length of stent 40 so that the surface area ($\gamma$) ultimately changes gradually or incrementally from one end of stent 40 to the other.

In another embodiment of the present invention, the drug concentration on the stents can be varied by selective application of the polymeric drug coating composition. For example, stent 40 can be selectively dipped in multiple repetitions so that the coating is less thick or absent from particular segments of stent 40. By using a selective dipping process, the thickness of the coating can gradually or incrementally increase from first end 48 to second end 50. Additionally, for example, a spray coater can be used to selectively apply the polymeric drug coating to stent 40 so that the thickness of the coating varies along the length of the stent. Masks, for example, can be placed along certain segments of the stent during a portion of the coating process, thereby blocking the composition ejected from the spray coater along these segments. By gradually moving the mask along the length of the stent during the spray application, the coating thickness can be gradually increased from first end 48 to second end 50.

In another embodiment, the drug concentration on the stents can be varied by changing the drug concentration in the composition during the coating process. For example, during a spraying process, the amount of a drug can be gradually increased in the composition while the composition is being sprayed onto the stent from one end of the stent to the other.

Methods of Varying the Release Rate

The release rate of the drug from the polymeric coating on the stent can be varied by using different approaches. As with the previous section, for ease of discussion, the following describes how to vary the release rate along the length of the stent. However, one of ordinary skill in the art will understand that these same approaches can also be used to vary the release rate along the circumference of the stent or along individual structural members such as struts.

The release rate of the drug from the polymeric coating can be varied along the length of the stent by varying the thickness of the coating. For example, if the thickness of the polymeric coating is gradually or incrementally decreased along the length of the stent while maintaining a constant drug concentration along the same length of stent, the release rate of the drug will gradually or incrementally increase over this length. For example, a stent coating could have a profile as described in Table I.

TABLE I

| Stent Segment | Coating Thickness (μm) | Drug Concentration (μg) | Drug Release Rate (μg/hour) |
|---|---|---|---|
| I (distal segment) | 20 | 100 | 1 |
| II (middle segment) | 15 | 100 | 1.5 |
| III (proximal segment) | 10 | 100 | 2 |

The drug release rate from the distal segment would be less than the release rate from the middle and proximal segments because the drug would have to diffuse through more polymer. The thickness of the coating can be varied while maintaining a constant drug concentration by varying the drug concentration during multiple spray applications in combination with a masking technique. For example, for the application of the coating of Table I, the following application process could be applied:

TABLE II

| Spray Application | Segment Masked | Coating Applied to Stent (μm) | Drug Concentration in the Composition |
|---|---|---|---|
| First | II and III | 20 | n |
| Second | I and III | 15 | 1.5n |
| Third | I and II | 10 | 2n |

The release rate of the drug from the polymeric coating can also be varied along the length of the stent by varying the thickness of particular regions of the coating. For example, the polymeric coating could have a reservoir region that contains the drug, and a diffusion barrier layer that is substantially free from drug and reduces the release rate of the drug from the coating. The release rate can be varied along the length of the stent by varying the thickness of the barrier layer along the length of the stent, for example, by masking portions of the stent during spray application.

The release rate can also be varied by using different polymers that have different drug permeabilities along the length of the stent. For example, if the reservoir layer is constructed of a polymer A (e.g., ethylene vinyl alcohol copolymer) that produces a higher release rate than a reservoir layer constructed of polymer B (with the same thickness) (e.g., polybutylmethacrylate), then the release rate can be varied by using pure polymer A at particular segments of stent 40 and pure polymer B at other segments. The release rate can be varied along the length of stent 40 by mixing varying amounts of polymer A and B along the length. One skilled in the art will understand that the release rate will be determined in part by the diffusion rate of the drug in the particular polymer or polymers used in the coating.

Embodiments of the Composition

The composition for the coating can include a solvent, a polymer dissolved in the solvent and a drug. The composition can be applied to the surface of the stent by any conventional means, and a final heat treatment can be conducted to remove essentially all of the solvent from the composition to form the coating.

Representative examples of polymers that can be used to coat a stent in accordance with the present invention include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; polybutylmethacrylate; rayon; rayon-triacetate; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Representative examples of solvents include chloroform, acetone, water (buffered saline), dimethylsulfoxide (DMSO), propylene glycol methyl ether (PM,) isopropylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof.

The drug contained in the coating can be for inhibiting the activity of vascular smooth muscle cells. More specifically, the drug can be aimed at inhibiting abnormal or inappropriate migration and/or proliferation of smooth muscle cells for the inhibition of restenosis. The drug can also include any substance capable of exerting a therapeutic or prophylactic effect in the practice of the present invention. For example, the drug can be for enhancing wound healing in a vascular site or improving the structural and elastic properties of the vascular site. Examples of drugs include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The drug can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany), methotrexate, azathioprine, vincristine, vinblastine, fluorouracil, doxorubicin hydrochloride (e.g. Adriamycin® from Pharmacia & Upjohn, Peapack, N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The dosage or concentration of the drug required to produce a favorable therapeutic effect should be less than the level at which the drug produces toxic effects and greater than the level at which non-therapeutic results are obtained. The dosage or concentration of the drug required to inhibit the desired cellular activity of the vascular region can depend upon factors such as the particular circumstances of the patient; the nature of the trauma; the nature of the therapy desired; the time over which the ingredient administered resides at the vascular site; and if other drugs are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Optional Coating Layers

An optional primer layer can be formed prior to the reservoir coating (i.e., the coating containing the drug) to increase the retention of the reservoir coating on the surface of the stent, particularly metallic surfaces such as stainless steel. The primer layer can act as an intermediary adhesive tie layer between the surface of the device and the reservoir coating, allowing for the quantity of the drug to be increased in the reservoir coating. In addition, an optional diffusion barrier can be formed over the reservoir coating to reduce the rate at which the drug is released from the coated stent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising a body having a first end and a second end and comprising a body coating including:
   a drug;
   a reservoir region containing the drug; and
   a barrier region disposed over the reservoir region, wherein
   a concentration of the drug in the coating increases along the stent body from the first end to the second end;
   a thickness of the barrier region decreases along the stent body from the first end to the second end; and
   the barrier region is completely or substantially drug-free.

2. The stent of claim 1 wherein a thickness of the coating increases along the stent body from the first end to the second end.

3. The stent of claim 1 wherein a surface area of the body increases along the stent body from the first end to the second end.

4. A method for forming the stent of claim 1 comprising forming a stent coating comprising:
   a drug;
   a reservoir region containing the drug; and
   a barrier region disposed over the reservoir region, wherein
   a concentration of the drug in the coating increases along the stent body from the first end to the second end;
   a thickness of the barrier region decreases along the stent body from the first end to the second end; and
   the barrier region is completely or substantially free of the drug.

5. The method of claim 4 wherein a thickness of the coating increases along the stent body from the first end to the second end.

6. The method of claim 4 wherein a surface area of the body increases along the stent body from the first end to the second end.

7. A stent having a body with a first end and a second end, the body comprising depots disposed in the stent body surface and filled with a drug and a barrier region, wherein
   the depot volume increases along the stent body from the first end to the second end,
   a thickness of the barrier region decreases along the stent body from the first end to the second end; and
   the barrier region is completely or substantially drug-free.

8. A stent comprising a body having a first end and a second end and comprising a body coating including:
   a drug,
   a reservoir region containing the drug; and
   a barrier region disposed over the reservoir region, wherein
   a release rate of the drug from the coating increases along the stent body from the first end to the second end,
   a permeability of the drug in the coating increases along the stent body from the first end to the second end;
   a thickness of the barrier region decreases along the stent body from the first end to the second end; and
   the barrier region is completely or substantially drug-free.

9. A method for forming a stent having a body with a first end and a second end, the method comprising applying a coating containing a drug to the stent surface, wherein a concentration of the drug in the coating and a permeability of the drug in the coating increase along the length of the stent body from the first end to the second end wherein a thickness of the coating increases along the length of the stent body from the first end to the second end.

10. A method for forming a stent having a body with a first end and a second end, the method comprising applying a coating containing a drug to the stent surface, wherein a concentration of the drug in the coating and a permeability of the drug in the coating increase along the length of the stent body from the first end to the second end wherein a surface area of the body increases along the stent body from the first end to the second end.

* * * * *